United States Patent [19]

Shimatani et al.

[11] Patent Number: 4,964,887
[45] Date of Patent: Oct. 23, 1990

[54] PROCESS FOR SEPARATING METHANE USING PERMEABLE MEMBRANE

[75] Inventors: Shunichi Shimatani; Michiharu Yamamoto; Akira Shimazu; Akio Iwama, all of Osaka, Japan

[73] Assignee: Nitto Denko Corporation, Osaka, Japan

[21] Appl. No.: 270,583

[22] Filed: Nov. 14, 1988

[30] Foreign Application Priority Data

Nov. 12, 1987 [JP] Japan .................. 62-286789
Dec. 23, 1987 [JP] Japan .................. 62-327843
Dec. 23, 1987 [JP] Japan .................. 62-327844
Feb. 23, 1988 [JP] Japan .................. 63-041657
Apr. 20, 1988 [JP] Japan .................. 63-097739

[51] Int. Cl.$^5$ .............................................. B01D 59/10
[52] U.S. Cl. ............................................ 55/16; 55/68; 585/818; 208/308
[58] Field of Search ................. 585/818; 55/16, 158, 55/68; 208/308; 428/473.5

[56] References Cited

U.S. PATENT DOCUMENTS 4,240,914 12/1980 Iwama et al. .................. 210/500.39
4,358,378 11/1982 Iwama et al. .................. 210/500.39
4,474,662 10/1984 Makino et al. ................... 55/158
4,474,858 10/1984 Makino et al. ................... 55/158
4,705,540 11/1987 Hayes ............................ 55/16

FOREIGN PATENT DOCUMENTS 0143552 10/1984 European Pat. Off. .
2849978 11/1977 Fed. Rep. of Germany .
2051664 5/1980 United Kingdom .
2073654 3/1981 United Kingdom .

*Primary Examiner*—Olik Chaudhuri
*Assistant Examiner*—George R. Fourson
*Attorney, Agent, or Firm*—Sughrue, Mion, Zinn, Macpeak & Seas

[57] ABSTRACT

A process for separating methane from a gaseous mixture containing methane and carbon dioxide by concentration is disclosed, which comprises contacting said gaseous mixture with a membrane comprising a film of a polyimide resin having a repeating unit represented by formula (I):

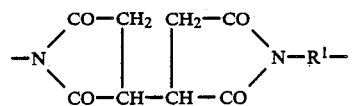

wherein R$^1$ represents a divalent aromatic, alicyclic or aliphatic hydrocarbon group, or a divalent organic group composed of these hydrocarbon groups linked via a divalent organic linking group. The membrane exhibits excellent selective permeability to carbon dioxide, enabling efficient and stable separation of methane.

25 Claims, No Drawings

PROCESS FOR SEPARATING METHANE USING PERMEABLE MEMBRANE

FIELD OF THE INVENTION

This invention relates to a process for separating methane by concentration using a selective permeable membrane. More particularly, it relates to a process for effectively separating methane from a gaseous mixture containing methane and carbon dioxide by the use of a membrane having selective permeability to carbon dioxide.

BACKGROUND OF THE INVENTION

Separation of methane by concentration of a gaseous mixture containing methane and carbon dioxide, such as natural gas, off-gas of oil field gas, blast furnace gas, burning furnace gas, etc., by means of a permeable membrane has been generally conducted at high temperature above 50° C. These gaseous mixtures mostly contain acidic gases, such as sulfur dioxide, hydrogen sulfide, etc., in addition to carbon dioxide. Therefore, the membrane to be used for separation of methane from such a gaseous mixture is required not only to have selective permeability to carbon dioxide but also to have heat resistance, acid resistance, and hydrocarbon resistance as well as mechanical strength.

Conventional membranes for separation of methane include composite membranes mainly comprising cellulose resins, e.g., cellulose acetate and ethyl cellulose. However, these membranes comprising cellulose resins are inferior in heat resistance and hydrocarbon resistance and it has been difficult, therefore, to stably separate methane by the use of these conventional membranes.

SUMMARY OF THE INVENTION

One object of this invention is to provide a process for separating methane by concentration by using a membrane excellent in permeability to carbon dioxide, heat resistance, acid resistance, hydrocarbon resistance, and mechanical strength.

As a result of extensive investigations, the inventors have found that methane can effectively be separated from a gaseous mixture containing methane and carbon dioxide by treating the gaseous mixture with a membrane comprising a polyimide resin obtained by reacting 1,2,3,4-butanetetracarboxylic acid and a diamine or with a composite film composed of the polyimide resin membrane as a supporting membrane and an elastomeric polymer film.

That is, the present invention relates to a process for separating methane from a gaseous mixture containing methane and carbon dioxide by concentration, which comprises contacting said gaseous mixture with a membrane comprising a polyimide resin having a repeating unit represented by formula (I):

$$-N\begin{matrix} CO-CH_2 & CH_2-CO \\ | & | \\ CO-CH-CH-CO \end{matrix}N-R^1-$$

wherein $R^1$ represents a divalent aromatic, alicyclic or aliphatic hydrocarbon group, or a divalent organic group composed of these hydrocarbon groups linked via a divalent organic linking group, to selectively pass carbon dioxide through said membrane.

The present invention further relates to a process for separating methane from a gaseous mixture containing methane and carbon dioxide by concentration, which comprises contacting said gaseous mixture with a composite membrane composed of the above-described polyimide resin membrane as a supporting film and a film comprising an elastomeric polymer to selectively pass carbon dioxide through said composite membrane.

DETAILED DESCRIPTION OF THE INVENTION

The membrane comprising the polyimide resin serves as a selective carbon dioxide-permeable membrane by itself and also as a supporting film of a composite membrane.

The membrane comprising the polyimide resin is known per se as described, e.g., in U.S. Pat. Nos. 4,240,914 and 4,358,378.

In formula (I), $R^1$ represents a divalent aromatic, alicyclic or aliphatic hydrocarbon group, or a divalent organic group composed of these hydrocarbon groups linked via a divalent organic linking group.

The divalent aromatic hydrocarbon group preferably includes phenylene groups having from 6 to 12 carbon atoms. The organic linking group which connects such divalent aromatic hydrocarbon groups to form a divalent organic group includes an alkylene group (e.g., methylene, isopropylidene), an ether group, a sulfido group, a sulfo group, an amido group, an ester group, an urethane group, a urea group, etc.

The divalent aliphatic hydrocarbon group preferably includes straight chain or branched alkylene groups having from 1 to 10 carbon atoms. The organic linking group which connects such divalent aliphatic hydrocarbon groups to form a divalent organic group includes an ether group, a sulfido group, an amido group, an ester group, a urethane group, a urea group, a polyoxyalkylene group, etc.

The divalent alicyclic hydrocarbon group preferably includes cyclohexylene groups having from 6 to 12 carbon atoms and alkyl-substituted cyclohexylene groups. The organic linking group which connects such divalent alicyclic hydrocarbon groups to form a divalent organic group includes an alkylene group (e.g., methylene, isopropylidene), an ether group, a sulfido group, a sulfo group, an amido group, an ester group, a urethane group, a urea group, etc.

From the standpoint of heat resistance and hydrocarbon resistance, the polyimide resin preferably includes those wherein $R^1$ represents an aromatic hydrocarbon group or an aromatic hydrocarbon group composed of two aromatic hydrocarbon groups connected by an organic linking group, such as an alkylene group (e.g., methylene, isopropylidene), an ether group, a sulfide group, a sulfo group, etc., more preferably those wherein $R^1$ represents an aromatic hydrocarbon group composed of two aromatic hydrocarbon groups connected via an alkylene group (e.g., methylene, isopropylidene) or an ether group, such as 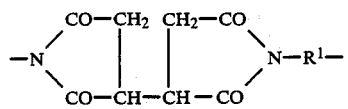 and

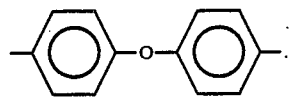

Also preferred is the polyimide resin of formula (I) wherein $R^1$ represents a divalent organic group containing a sulfo group. Examples of such a divalent organic group are groups represented by formula (II):

$$-R^2-SO_2-R^3- \qquad (II)$$

wherein $R^2$ and $R^3$ each represents a divalent aromatic, alicyclic or aliphatic hydrocarbon group, or a divalent organic group composed of these hydrocarbon groups linked via a divalent organic linking group.

In formula (II), the divalent aromatic hydrocarbon group as represented by $R^2$ or $R^3$ preferably includes phenylene groups having from 6 to 12 carbon atoms, and the organic linking group which connects such divalent aromatic hydrocarbon groups to form a divalent organic group, includes an alkylene group (e.g., methylene, isopropylidene), an ether group, and a sulfido group.

The divalent aliphatic hydrocarbon group as represented by $R^2$ or $R^3$ preferably includes straight chain or branched alkylene groups having from 1 to 10 carbon atoms, and the organic linking group which connects such divalent aliphatic hydrocarbon groups to form a divalent organic group includes an ether group, a sulfido group, and a polyoxyalkylene group.

The divalent alicyclic hydrocarbon group as represented by $R^2$ or $R^3$ preferably includes cyclohexylene groups having from 6 to 12 carbon atoms and alkyl-substituted cyclohexylene groups, and the organic linking group which connects such divalent alicyclic hydrocarbon groups to form a divalent organic group includes a methylene group, an isopropylidene group, an ether group, and a sulfido group.

From the standpoint of heat resistance and hydrocarbon resistance, more preferred of the polyimide resins containing a divalent organic group of formula (II) are those wherein both $R^2$ and $R^3$ represent an aromatic hydrocarbon group or an aromatic hydrocarbon group composed of two aromatic hydrocarbon groups linked via an organic linking group, such as an alkylene group (e.g., methylene, isopropylidene), an ether group, and a sulfido group.

Specific examples of the most preferred group of formula (II) are

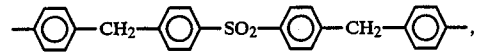

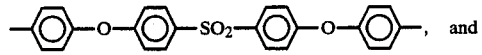 and

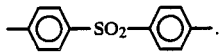

In order that these polyimide resins may exhibit excellent film-forming properties in the wet film formation process hereinafter described and also that the resulting film may have sufficient mechanical strength, it is desirable that the resins have an intrinsic viscosity $[\eta]$ of from 0.4 to 2 dl/g, more preferably from 0.4 to 1 dl/g, as measured in N-methyl-2-pyrrolidone at 30° C. (hereinafter the same).

When a gaseous mixture containing methane and carbon dioxide is brought into contact with the above-stated polyimide resin having a sulfo group in the molecule thereof as a separating membrane, a very high rate of permeation to carbon dioxide is achieved. It is assumed to be because the solubility of carbon dioxide in the membrane is enhanced by the sulfo group of the resin, but it should be understood that the present invention is by no means limited by the theory.

The polyimide resin membrane to be used as a selective permeable membrane, by itself or as a supporting membrane of a composite membrane can preferably be prepared in accordance with the following wet process.

A film forming solution comprising the polyimide resin having the repeating unit of formula (I) and a water-miscible organic solvent (hereinafter referred to as a first organic solvent) is prepared. The solution is coated on an appropriate base and then dipped in an organic solvent incapable of dissolving the polyimide resin but miscible with either of the first organic solvent and water (hereinafter referred to as a second organic solvent) for a short time. Thereafter, the film on the base is dipped in water to obtain a water-containing polyimide membrane having an anisotropic structure, which is then dried by an appropriate means to thereby obtain a membrane having an anisotropic structure having a so-called skin layer.

Specific examples of the first organic solvent to be used in the film-forming solution include an N-alkyl-2-pyrrolidone (e.g., N-methyl-2-pyrrolidone), an N-alkyl-2-piperidone (e.g., N-methyl-2-piperidone), a dialkylacetamide (e.g., dimethylacetamide), and a dialkylformamide (e.g., dimethylformamide), with N-methyl-2pyrrolidone being preferred.

The concentration of the polyimide resin in the film-forming solution usually ranges from 10 to 40% by weight, preferably from 15 to 30% by weight. If it is too high, the excessive viscosity of the solution makes it difficult to uniformly apply the solution on a base and, in addition, the resulting membrane has poor permeability to carbon dioxide for practical use. In connection with the polyimide resin concentration, the viscosity of the film-forming solution is usually adjusted to a range of from 50 to 5,000 poise, preferably from 100 to 2,000 poise.

The film-forming solution is coated on the base to a thickness usually of from 50 to 400 μm, preferably from 100 to 300 μm. Too a thin film only produces a membrane failing to have a practical strength. If the film thickness is too large, the resulting membrane is of no utility due to low rate of gas permeation, though high in separation selectivity.

The base to be used for film formation includes sheets having a smooth surface, such as a glass plate, a stainless steel sheet, a resin sheet, etc., and woven or non-woven cloth. Membranes obtained by using woven or non-woven cloth as a base are advantageous because of enhanced strength.

Specific examples of the second solvent incapable of dissolving the polyimide resin but miscible with either of the first organic solvent and water include lower aliphatic alcohols (e.g., methanol, ethanol, propanol, butanol), alcohols having a cyclic structure (e.g., furfuryl alcohol, tetrahydrofurfuryl alcohol), ketones (e.g., acetone, methyl ethyl ketone, diacetone alcohol), esters of formic acid, acetic acid, lactic acid, phosphoric acid, etc.; polyhydric alcohols (e.g., ethylene glycol, propylene glycol, dipropylene glycol, trimethylene glycol, butanediol, glycerin, pentanediol, hexylene glycol, diethylene glycol, triethylene glycol, tetraethylene glycol) and derivatives thereof such as ethers and esters (e.g., methyl cellosolve, cellosolve acetate, butyl cellosolve, methylcarbitol, butylcarbitol, carbitol acetate, dipropylene glycol monomethyl ether, butoxyethoxypropanol, propylene glycol monomethyl ether, triethylene glycol monomethyl ether); ethers (e.g., dioxane, tetrahydrofuran); and nitriles (e.g., acetonitrile). These solvents may be used either individually or in combinations of two or more thereof.

The dipping in the second organic solvent is usually effected at a temperature of from 0° to 100° C. for 1 hour or less, preferably 5 minutes or less.

After the film is dipped in the second organic solvent, it is dipped in water usually at a temperature of from 0° to 50° C., preferably from 0° to 30° C., more preferably from 0° to 20° C., to obtain a water-containing membrane having anisotropy.

Thereafter, the resulting water-containing membrane is dipped in an organic solvent having miscibility with either water and an organic solvent, e.g., alcohols, and then in an organic solvent immiscible with water, e.g., hexane, followed by drying at room temperature or, if necessary, under heating to obtain a dried membrane possessing selective gas permeability. The method for drying the water-containing membrane is not limited to the above-described one.

The thus obtained membrane can be used as it is for separation of methane by concentration. The membrane can also be used as a supporting membrane on which a thin film of an elastomeric polymer is formed.

In a preferred embodiment of the above-described wet film formation process, the film-forming solution further contains a liquid swelling agent. A membrane prepared therefrom has further increased permeability to carbon dioxide.

The liquid swelling agent which can be used in this preferred embodiment is at least one liquid organic compound having a flocculation value for the polyimide resin according to the present invention ranging from 50 to 200 and having a boiling point of from 50° to 120° C. at atmospheric pressure which is selected from the group consisting of cyclic ethers, aliphatic ketones, alicyclic ketones, lower aliphatic carboxylic acids, and lower aliphatic carboxylic acid lower alkyl esters.

The terminology "flocculation value of a swelling agent for the polyimide resin" as used herein means a minimum number of milliliters of the swelling agent necessary to make 50 ml of a 2 wt % solution of the polyimide resin in N-methylpyrrolidone become white turbid at 25° C. due to flocculation of the resin.

The swelling agent should be soluble in both the first organic solvent and water and have a flocculation value for the polyimide resin of from 50 to 200 and a boiling point of from 50° to 120° C. at atmospheric pressure.

Specific and preferred examples of such a swelling agent are tetrahydrofuran, dioxane, acetone, methyl ethyl ketone, diethyl ketone, cyclohexanone, acetic acid, formic acid, methyl formate, ethyl formate, and methyl acetate. The swelling agent is added to the film-forming solution in an amount of from 30 to 300 parts by weight, preferably from 50 to 150 parts by weight, per 100 parts by weight of the polyimide resin. Too large and amount of the swelling agent sometimes hinders uniformity of the film-forming solution. If the amount of the swelling agent is too small, effects as expected cannot be produced.

The swelling agent can be incorporated into the film-forming solution, for example, by previously adding to a solution of the polyimide resin and stirring the mixture at room temperature or, if necessary, under heating.

The membrane prepared from the film-forming solution containing the above-described swelling agent is the most preferred for use as a selective permeable membrane either by itself or in combination with an elastomeric polymer film for separation of methane by concentration.

In the former case, when a gaseous mixture containing methane and carbon dioxide is brought into contact with the selective permeable membrane, the carbon dioxide selectively passes through the membrane to thereby obtain a gaseous mixture comprising concentrated methane in the side to which the gaseous mixture to be treated is fed and a gaseous mixture comprising concentrated carbon dioxide in the side into which carbon dioxide passes. If desired, the gaseous mixture containing methane in high concentration can be subjected to further processing, such as compression, adsorption, condensation and the like, to separate methane therefrom.

The polyimide resin membrane according to the present invention essentially has a high permeability to carbon dioxide and a coefficient of $CO_2/CH_4$ separation as high as 100 or even more. However, when it is formed into a thin film suited for separation of methane by concentration, the membrane sometimes unavoidably suffers from defects or pinholes. Therefore, it is not always easy to stably obtain a thin membrane having such a high coefficient of separation on an industrial scale.

In this connection, it is preferable in the present invention that the membrane comprising the polyimide resin be used as a supporting membrane on which a thin film of an elastomeric polymer is provided to obtain a composite membrane for separation of methane. That is, the composite film can achieve separation of methane from a gaseous mixture containing carbon dioxide with great advantages at an extremely high coefficient of $CO_2/CH_4$ separation while stably retaining a high rate of permeation to carbon dioxide. The polyimide resin membrane serving as a support for the composite membrane preferably has a coefficient of $CO_2/CH_4$ separation of at least 0.7, and particularly at least 0.9.

The composite membrane according to the present invention can be produced by forming a thin film of an elastomeric polymer on the dense skin layer of the polyimide resin supporting membrane.

The elastomeric polymer which can be used is a polymer capable of forming a soft film. Typical examples of such an elastomeric polymer include homo- or copolymers of ethylenically unsaturated monomers or conjugated diene monomers, such as polypropylene, polyvinyl chloride, an ethylene-propylene copolymer, an ethylene-propylene-diene copolymer, polybutadiene, polyisoprene, chloroprene rubber, poly(4-methyl-penten-1), a butadiene-styrene copolymer, an isoprene-isobutylene copolymer, and polyisobutylene. Copolymers comprising the above-enumerated monomers and compolymerizable monomers having a functional group, such as acrylonitrile, (meth)acrylic esters, and (meth)acrylic acid, can also be used preferably. Preferred among these polymers are homo- or copolymers of ethylenically unsaturated monomers or conjugated diene monomers.

In addition, silicone resins are also preferred as an elastomeric polymer. In particular, a film obtained by crosslinking a crosslinkable silicone resin is preferred.

Further implicit in the elastomeric polymer to be used in the composite membrane are copolymers having both soft segments and hard segments, such as polyester polyol, polyurethane polyether, polyurethane polyester, and polyamide polyether. Specific examples of such copolymers are shown below:

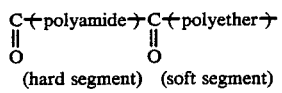
(hard segment) (soft segment)
(1)

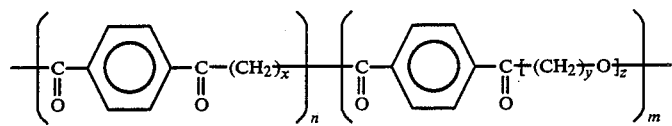
(hard segment) (soft segment)
[x: 1 to 4; y: 1 to 10; z: 1 to 100; n, m: degree of polymerization of from 10 to 10,000]
(2)

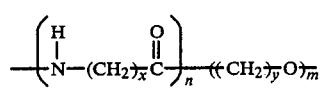
(hard segment) (soft segment)
[x: 1 to 5; n, m: degree of polymerization of from 10 to 10,000]
(3)

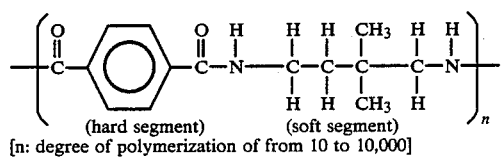
(hard segment) (soft segment)
[n: degree of polymerization of from 10 to 10,000]
(4)

Furthermore, epoxy resins curable by a straight long chain curing agent, ethyl cellulose, and butoxy resins are also employable as elastomeric polymer. The above-described elastomeric polymers having introduced into the molecular chain or terminals thereof a functional group, e.g., a carboxyl group, a hydroxyl group, a hydroxyalkyl group, an amido group, an amino group, an alkoxy group, etc. are also preferred.

These elastomeric polymers preferably have a coefficient of $CO_2/CH_4$ separation of at least 3 and a softening point of at least 50° C., particularly at least 80° C.

The composite membrane according to the present invention can be obtained by dissolving the elastomeric polymer in an appropriate organic solvent and coating the solution on the dense skin layer of the supporting membrane comprising the polyimide resin, if necessary curing the coating film, and drying.

The elastomeric polymer solution usually has a concentration of from 0.05 to 10% by weight, preferably from 0.1 to 5% by weight. The elastomeric polymer solution is coated on the supporting membrane to a thickness of from 0.01 to 5 μm, preferably from 0.05 to 1 μm. The coating means is not particularly restricted and includes an applicator, a microgravure coater, etc. The coating may be carried out by dipping the supporting membrane in the elastomeric polymer solution.

In the present invention, it is preferable that the elastomeric polymer on the polyimide supporting membrane be crosslinked by an appropriate means. Namely, the composite membrane of the invention preferably comprises the polyimide resin supporting membrane having formed thereon a crosslinked elastomeric polymer film.

The gaseous mixture containing methane generally contains petroleum hydrocarbons, and in most cases, aliphatic hydrocarbons having 3 or more carbon atoms that are approximately the same with crude oil. By the use of the composite membrane having the crosslinked elastomeric polymer film, methane can efficiently be separated from a gaseous mixture without involving swelling of the membrane or reduction in separation performance due to the petroleum hydrocarbons even in long-term treatment.

Crosslinking of the elastomeric polymer film on the supporting membrane can be carried out typically by using a crosslinking agent or irradiating an electron beam on the elastomeric polymer film.

The process using a crosslinking agent is effected by coating a solution containing the elastomeric polymer and a crosslinking agent on the surface of the supporting membrane, and then heating the elastomeric polymer film to induce crosslinking. It is essential that the crosslinking agent should not cause crosslinking reaction of the elastomeric polymer during the coating until heated. If a crosslinking agent working at room temperature is used, the elastomeric polymer precipitates in the coating solution or undergoes gelation due to crosslinking during coating, thus failing to form a thin and uniform membrane excellent in gas permeability.

Included in the crosslinking agents satisfying the above-stated requirement are, for example, radical generators, e.g., benzoyl peroxide, methyl ethyl ketone peroxide, cumene hydroperoxide, azobisisobutyronitrile, etc.

When the elastomeric polymer contains a functional group, e.g., a carboxyl group, a hydroxyl group, a hydroxyalkyl group, an amido group, an amino group, an alkoxy group, etc., in the molecule thereof or at the terminals thereof as mentioned above, a compound having a polyfunctional group capable of reacting with such a functional group, e.g., polyisocyanate, is preferably used as a crosslinking agent.

In addition, when the elastomeric polymer contains a carboxyl group, it may be ion-crosslinked in the presence of a polyvalent metallic ion, e.g., aluminum, calcium, magnesium, copper, barium or zinc ion. In this case, too, the polyvalent metallic ion to be used should be selected from those which do not cause crosslinking at room temperature but are reacted with the functional group of the elastomeric polymer upon heating.

Radiation to be used for crosslinking the elastomeric polymer film is not particularly limited as far as it is ionizing radiation and includes, for example, electron rays, neutron rays, α-rays, β-rays, γ-rays, and ultraviolet rays. The irradiation dose usually ranges from 1 to 50 Mrad, preferably from 3 to 20 Mrad, though varying depending on the temperature, pressure, etc. of the irradiation atmosphere.

The irradiation induces radical generation in the side chain of the polymer, and the radical molecules are mutually crosslinked to form a crosslinked film on the supporting membrane.

Whichever crosslinking process may be selected, the degree of crosslinking should be properly selected so as not to cause swelling or dissolution of the crosslinked film with petroleum hydrocarbons present in the gaseous mixture to be treated and is suitably determined in accordance with the kind of the elastomeric polymer or the crosslinking process adopted. Excessive crosslinking would rather impair properties of the elastomeric polymer, causing cracks of the resulting composite membrane.

The elastomeric polymer solution has a polymer concentration usually of from 0.05 to 10% by weight, preferably from 0.1 to 5% by weight. The solution is usually coated on the supporting membrane to a film thickness of from 0.01 to 5 μm, preferably from 0.05 to 1 μm. The coating means includes an applicator, a microgravure coater, etc. The coating may be effected by dipping the supporting membrane in the elastomeric polymer solution.

The composite membrane having a crosslinked silicone resin as a crosslinked elastomeric polymer can be obtained by crosslinking a crosslinkable silicone resin film formed on the supporting membrane. The crosslinkable silicone resin is a silicone resin which is soluble in organic solvents before crosslinking but provides an organic solvent-insoluble resin on crosslinking. Such a crosslinkable silicone resin carries various reactive groups at each of the molecular chain terminals, by which the molecules are mutually crosslinked in the presence or absence of a crosslinking agent or a curing agent.

More specifically, the crosslinkable silicone resin which can be used in the present invention is generally represented by formula:

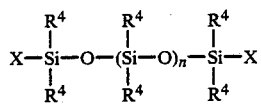

or formula:

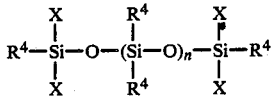

wherein X represents a reactive group; and $R^4$ represents an alkyl or aryl group; and a part of the repeating unit may be replaced by a group represented by formula:

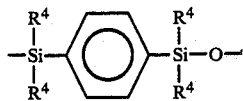

wherein $R^4$ is as defined above.

In the above formulae, the reactive group as represented by X includes a vinyl group, an acryloxyalkyl group, a methacryloxyalkyl group, a hydroxyl group, a hydroxyalkyl group, an acyloxy group, an alkoxy group, an aminoalkyl group, a carboxylalkyl group, a ketoxime group, an alkylamino group, an amido group, etc. A part of $R^4$ may be replaced with such a reactive group. $R^4$ typically includes a methyl group and a phenyl group.

Various kinds of the crosslinkable silicone resin having the above-enumerated reactive groups are already known and are available as commercial products.

If desired, crosslinking of the crosslinkable silicone resin having reactive groups at the molecular terminals thereof may be carried out in the presence of a crosslinking agent, a curing agent, or a polymerization initiator. For example, in case of using vinyl-terminated organopolysiloxane or (meth)acryloxy-alkyl-terminated organopolysiloxane, a radical generator is employed as a crosslinking agent. Examples of such a radical generator are organic peroxides, e.g., benzoyl peroxide, methyl ethyl ketone peroxide, cumene hydroperoxide, etc., and azo compounds, e.g., azobisisobutyronitrile, etc. In case of using crosslinkable silicone resins having a hydroxyl group, a hydroxyalkyl group, an acyloxy group, an alkoxy group, an alkylamino group, an amido group, a ketoxime group, etc. as a reactive group, crosslinking can be induced by water content in the atmosphere. In case of using crosslinkable silicone resins having an aminoalkyl group, a carboxyalkyl group, a hydroxyl group, a hydroxyalkyl group, etc. as a reactive group, a bi- or polyfunctional polyisocyanate or an epoxy resin is preferably used as a curing agent. The polyisocyanate includes tolylene diisocyanate, m-xylylene diisocyanate, 4,4'-diphenylmethane diisocyanate, polytetramethylene glycol diisocyanate, polypropylene glycidyl diisocyanate, etc. In case of using crosslinkable silicone resins having an acyloxy group, an alkoxy group, a ketoxime group, an alkylamino group, an amido group, etc. as a reactive group, crosslinking can easily be induced by polyhydric alcohols. The polyhydric alcohols include ethylene glycol, propylene glycol, butylene glycol, pentanediol, hexanediol, diethylene glycol, dipropylene glycol, triethylene glycol, glycerin, etc. Of these polyhydric alcohols, glycerin or triethyelne glycol is particularly useful since it can induce crosslinking of the crosslinkable silicone resin at ambient temperature without requiring heating. The polyhydric alcohol may be incorporated into the solution of the crosslinkable silicone resin as in the case of one-can curable resins.

If an organic solution of the crosslinkable silicone resin applied onto the skin layer of the supporting membrane penetrates into the inside of the supporting membrane, a dense crosslinked silicone resin is formed also in the inside of the polyimide membrane, thereby providing a dense layer having an increased thickness. To this effect, it is desirable that the crosslinkable silicone resin to be used be chosen so as to have an average molecular weight equal to or larger than the fractional molecular weight of the polyimide supporting membrane. Usually, a crosslinkable silicone resin having an average molecular weight of from 10,000 to 300,000 as determined by gel-permeation chromatography is preferred. The crosslinkable silicone resin having such a molecular weight range is implicit in the silicone resins having the above-described formula wherein n is between 100 and 4,000.

The organic solvent to be usd for dissolving the crosslinkable silicone resin is not particularly limited and can be selected appropriately, depending on the kind of the resin, from aliphatic hydrocarbons, aromatic hydrocarbons, alcohols, carboxylic acids, esters, ketones, ethers, halogenated hydrocarbons, and the like.

The solution of the crosslinkable silicone resin usually has a concentration of from 0.05 to 10% by weight, preferably from 0.1 to 5% by weight and is coated on the supporting membrane to a film thickness of from 0.01 to 5 $\mu$m, preferably from 0.05 to 1 $\mu$m. The coating can be carried out by means of an applicator, a microgravure coater, etc. or by dipping the supporting membrane in the crosslinkable silicone resin solution.

If necessary or depending on the kind of the organic solvent used, the solvent is removed at an appropriate temperature, for example, at room temperature up to about 80° C. The crosslinkable silicone resin is then crosslinked in the presence or absence of a crosslinking agent, a curing agent or a radical initiator to form a three-dimensional structure. If necessary, the crosslinking temperature may be higher than the above-recited temperature.

The thus formed crosslinked silicone resin film preferably has a coefficient of $CO_2/CH_4$ separation of at least 3.

For the purpose of increasing crosslinking density, the crosslinked silicone resin film may be irradiated with ionizing radiation, such as electron rays, neutron rays, $\alpha$-rays, $\beta$-rays, $\gamma$-rays, ultraviolet rays, etc. The irradiation dose usually ranges from 1 to 50 Mrad, preferably from 3 to 20 Mrad, though varying depending on the temperature or pressure of the atmosphere. By this irradiation, radicals are produced in the side chains of the crosslinked silicone resin, and these radical molecules are mutually crosslinked to thereby increase the crosslinking density, which leads to further improvements in mechanical strength, resistance to organic solvents, and selective permeability.

The thus obtained composite membrane comprising the polyimide membrane and an elastomeric polymer film can be used as a selective permeable membrane for separation of methane in the same manner as described for the polyimide membrane. If desired, the resulting gaseous mixture containig concentrated methane may be subjected to further processing, such as compression, adsorption, condensation and the like, to separate methane therefrom.

The selective permeable membrane according to the present invention is usually and preferably used in the form of a so-called spiral membrane module in which the web of the membrane is spirally wound. The membrane is also used as a module having a hollow yarn structure or other modular structure.

Since the polyimide resin membrane or a composite membrane using the polyimide resin membrane as a support is excellent not only in selective permeability to carbon dioxide but also in resistance to heat and hydrocarbons, the present invention makes it possible to stably separate methane from a gaseous mixture containing carbon dioxide together with methane.

The present invention is now illustrated in greater detail by way of the following Examples and Comparative Examples, but it should be understood that the present invention is not deemed to be limited thereto. In these examples, all the percents and parts are by weight unless otherwise indicated.

EXAMPLE 1

A 16% N-methyl-2-pyrrolidone solution of polyimide having a repeating unit of formula:

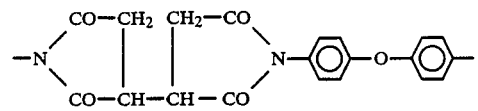

(intrinsic viscosity [$\eta$]: 0.79 dl/g) was coated on polyester non-woven cloth to a thickness of 200 $\mu$m. The coated cloth was dipped in an organic solvent shown in Table 1 under indicated conditions and then in water at 3° C. to obtain a water-containing membrane having an anisotropic structure (Sample Nos. 101 to 120)

Each of the resulting water-containing membranes was soaked first in ethanol and then in hexane for 3 hours, respectively, followed by air-drying at 25° C. to obtain a dried membrane.

A rate of permeation to carbon dioxide and a coefficient of $CO_2/CH_4$ separation of the membrane were determined, and the results obtained are shown in Table 1.

TABLE 1

| Sample No. | Solvent Dipping Conditions | | | Rate of Permeation to Carbon Dioxide ($Nm^3/m^2 \cdot hr \cdot atom$) | Coefficient of $CO_2/CH_4$ Separation |
|---|---|---|---|---|---|
| | Organic Solvent | Temp. (°C.) | Time (sec) | | |
| 101 | isopropyl alcohol | 3 | 10 | $1.9 \times 10^{-1}$ | 40 |
| 102 | " | " | 60 | $0.8 \times 10^{-1}$ | 70 |
| 103 | " | 20 | 10 | $1.4 \times 10^{-1}$ | 42 |
| 104 | " | " | 60 | $0.5 \times 10^{-1}$ | 82 |
| 105 | ethylene glycol | 3 | 10 | $4.1 \times 10^{-1}$ | 15 |
| 106 | " | " | 60 | $4.6 \times 10^{-1}$ | 14 |
| 107 | " | 20 | 10 | $6.3 \times 10^{-1}$ | 3 |
| 108 | " | " | 60 | $5.7 \times 10^{-1}$ | 15 |
| 109 | tetrahydrofuran | 3 | 10 | $11 \times 10^{-1}$ | 12 |

TABLE 1-continued

| Sample No. | Solvent Dipping Conditions | | | Rate of Permeation to Carbon Dioxide ($Nm^3/m^2 \cdot hr \cdot atom$) | Coefficient of $CO_2/CH_4$ Separation |
|---|---|---|---|---|---|
| | Organic Solvent | Temp. (°C.) | Time (sec) | | |
| 110 | " | " | 60 | $11 \times 10^{-1}$ | 11 |
| 111 | " | 20 | 10 | $11 \times 10^{-1}$ | 15 |
| 112 | " | " | 60 | $12 \times 10^{-1}$ | 14 |
| 113 | acetone | 3 | 10 | $8.8 \times 10^{-1}$ | 12 |
| 114 | " | " | 60 | $4.9 \times 10^{-1}$ | 23 |
| 115 | " | 20 | 10 | $6.8 \times 10^{-1}$ | 17 |
| 116 | " | " | 60 | $5.2 \times 10^{-1}$ | 30 |
| 117 | t-butanol | 25 | 10 | $2.7 \times 10^{-1}$ | 42 |
| 118 | " | " | 60 | $1.9 \times 10^{-1}$ | 53 |
| 119 | " | 45 | 3 | $2.2 \times 10^{-1}$ | 51 |
| 120 | " | " | 10 | $1.4 \times 10^{-1}$ | 41 |

EXAMPLE 2

A dried polyimide resin membrane was prepared in the same manner as in Example 1, except that the polyimide solution further contained a prescribed amount of a swelling agent as shown in Table 2 below.

A rate of permeation to carbon dioxide and a coefficient of $CO_2/CH_4$ separation of each of the resulting membranes (Sample Nos. 201 to 212) were determined, and the results obtained are shown in Table 2.

TABLE 2

| Sample No. | Swelling Agent | | | Rate of Permeation to Carbon Dioxide ($Nm^3/m^2 \cdot hr \cdot atom$) | Coefficient of $CO_2/CH_4$ Separation |
|---|---|---|---|---|---|
| | Kind | Flocculation Value | Amount Added (part*) | | |
| 201 | acetone | 63 | 25 | $1.9 \times 10^{-1}$ | 41 |
| 202 | " | " | 50 | $2.2 \times 10^{-1}$ | 43 |
| 203 | " | " | 100 | $1.1 \times 10^{-1}$ | 21 |
| 204 | " | " | 200 | $1.4 \times 10^{-1}$ | 33 |
| 205 | dioxane | 170 | 25 | $2.5 \times 10^{-1}$ | 55 |
| 206 | " | " | 50 | $2.7 \times 10^{-1}$ | 52 |
| 207 | " | " | 100 | $3.3 \times 10^{-1}$ | 66 |
| 208 | " | " | 200 | $4.4 \times 10^{-1}$ | 50 |
| 209 | tetrahydrofuran | 88 | 25 | $4.9 \times 10^{-1}$ | 21 |
| 210 | " | " | 50 | $6.3 \times 10^{-1}$ | 44 |
| 211 | " | " | 100 | $4.7 \times 10^{-1}$ | 25 |
| 212 | " | " | 200 | $6.8 \times 10^{-1}$ | 37 |

Note:
*per 100 parts by weight of the polyimide resin

EXAMPLE 3

To the same polyimide resin solution as used in Example 1 was added 50 parts of dioxane (flocculation value: 170) as a swelling agent per 100 parts of the polyimide resin to form a film-forming solution.

The solution was coated to polyester non-woven cloth to a thickness of 200 μm. The coated cloth was dipped in isopropanol at 3° C. for 10 seconds and then in water at 3° C. to obtain a water-containing membrane having an anisotropic structure.

The resulting water-containing membrane was soaked first in ethanol and then in hexane for 3 hours, respectively, followed by air-drying at 25° C. to obtain a dried membrane.

On the dried membrane was coated a solution of an elastomeric polymer shown in Table 3 below to a thickness of 30 μm, followed by drying at 80° C. for 30 minutes to prepare a composite membrane (Sample Nos. 301 to 304).

A rate of permeation to carbon dioxide and a coefficient of $CO_2/CH_4$ separation of the resulting composite membrane are shown in Table 3.

TABLE 3

| | Elastomeric Polymer Solution | | | Coefficient of $CO_2/CH_4$ Separation of Elastomeric Polymer | Composite Membrane | |
|---|---|---|---|---|---|---|
| Sample No. | Elastomeric Polymer | Solvent | Concn. (wt %) | | Rate of Permeation to Carbon Dioxide ($Nm^3/m^2 \cdot hr \cdot atm$) | Coefficient of $CO_2/CH_4$ Separation |
| 301 | poly(4-methylpentene-1) | cyclohexane | 1.0 | 5.4 | $2.2 \times 10^{-1}$ | 141 |
| 302 | butadiene-styrene copolymer | toluene | 1.0 | 18 | $2.0 \times 10^{-1}$ | 113 |
| 303 | polyisobutylene | isooctane | 0.5 | 11 | $1.0 \times 10^{-1}$ | 73 |
| 304 | isoprene-isobutylene copolymer | toluene | 1.0 | 12 | $2.5 \times 10^{-1}$ | 44 |

EXAMPLE 4

A composite membrane (Sample Nos. 401 to 406) was obtained in the same manner as in Example 3, except that an elastomeric polymer solution shown in Table 4 was used. In the preparation of Sample Nos. 405 and 406, the conditions for film formation on the supporting membrane were altered according to the kind of the elastomeric polymer as described in the footnote of Table 4.

A rate of permeation to carbon dioxide and a coefficient of $CO_2/CH_4$ separation of each of the resulting composite membranes are shown in Table 4.

The composite membrane was immersed in petroleum benzine at room temperature for about 30 hours and then in gasoline for about 30 hours. After washing with hexane, the membrane was dried. $P(CO_2)$ and $\alpha$ of the thus treated composite membrane were determined, and the results are shown in Table 6.

For comparison, composite membranes (Samples A to C) were prepared in the same manner as for Samples

TABLE 4

| | Elastomeric Polymer Solution | | | Coefficient of $CO_2/CH_4$ Separation of Elastomeric Polymer | Composite Membrane | |
|---|---|---|---|---|---|---|
| | | | | | Rate of Permeation to Carbon Dioxide | Coefficient |
| Sample No. | Elastomeric Polymer | Solvent | Concn. (wt %) | | ($Nm^3/m^2 \cdot hr \cdot atom$) | of $CO_2/CH_4$ Separation |
| 401 | polyester polyol | chloroform | 1.0 | 10 | $0.5 \times 10^{-1}$ | 74 |
| 402 | polyurethane polyol | tetrahydrofuran | 1.0 | 11 | $2.1 \times 10^{-1}$ | 61 |
| 403 | polyurethane polyester | tetrahydrofuran | 1.0 | 19 | $0.8 \times 10^{-1}$ | 80 |
| 404 | polyamide polyether | chloroform | 0.5 | 9 | $1.7 \times 10^{-1}$ | 105 |
| 405 | epoxy resin* | toluene | 5.0 | 15 | $0.2 \times 10^{-1}$ | 114 |
| 406 | ethyl cellulose** | chloroform | 2.0 | 18 | $1.0 \times 10^{-1}$ | 99 |

Note:
*Comprised 100 parts of Epon 828 (made by Shell Chemical), 10 parts of a curing agent CIBN (carboxyl-terminated butadiene-acrylonitrile copolymer), and 5 parts of tetramethylguanidine; Curing Conditions: heating at 180° C. for 1 hour.
**Heated at 60° C. for 30 minutes.

EXAMPLE 5

The same polyimide resin solution as used in Example 1 was prepared, and 50 parts of dioxane (flocculation value: 170) was dissolved therein as a swelling agent per 100 parts of the polyimide resin to prepare a film-forming solution.

The solution was coated on polyester non-woven cloth to a thickness of 200 μm. The coated cloth was dipped first in isopropanol at 3° C. for 10 seconds and then in water at 3° C. to obtain a water-containing membrane having an anisotropic structure.

The water-containing membrane was soaked successively in ethanol and then in hexane for 3 hours, respectively, followed by air-drying at 25° C. to prepare a supporting membrane.

An elastomeric polymer solution containing a radical generator or polyisocyanate as a crosslinking agent as shown in Table 5 was coated on the supporting membrane to a thickness of 30 μm and dried at 120° C. for 10 minutes to obtain a composite membrane having a crosslinked elastomeric polymer film (Sample Nos. 501 to 503).

Each of the resulting composite membranes was determined for rate of permeation to carbon dioxide $[P(CO_2)]$ and coefficient of $CO_2/CH_4$ separation ($\alpha$), and the results obtained are shown in Table 6.

501 to 503, except that the elastomeric polymer solution contained no crosslinking agent. $P(CO_2)$ and $\alpha$ of these comparative composite membranes were determined either before and after immersion in solvents in the same manner as described above, and the results obtained are also shown in Table 6.

TABLE 5

| | Elastomeric Polymer Solution | | | | |
|---|---|---|---|---|---|
| Sample No. | Elastomeric Polymer | Solvent | Concn. (wt %) | Crosslinking Agent | (Amount: part*1) |
| 501 | polyisobutylene*2 | toluene | 1.0 | benzoyl peroxide | (1.0) |
| 502 | butadiene-styrene copolymer*3 | " | 2.0 | " | (1.0) |
| 503 | polyurethane polyester*4 | " | 1.0 | triphenylmethane triisocyanate | (0.5) |

Note:
*1 Per 100 parts by weight of the elastomeric polymer.
*2 Opanol B100 produced by GASF
*3 Buna S produced by Bayer A.G.
*4 Pandex produced by Dai-Nippon Ink & Chemicals, Inc.

TABLE 6

| | Gas Permeability of Composite Membrane | | | |
|---|---|---|---|---|
| | Before Solvent Immersion | | After Solvent Immersion | |
| Sample No. | $P(CO_2)$ ($Nm^3/m^2 \cdot hr \cdot atm$) | $\alpha$ | $P(CO_2)$ ($Nm^3/m^2 \cdot hr \cdot atm$) | $\alpha$ |
| 501 | $0.8 \times 10^{-1}$ | 69 | $0.8 \times 10^{-1}$ | 69 |
| 502 | $1.8 \times 10^{-1}$ | 150 | $1.8 \times 10^{-1}$ | 147 |
| 503 | $1.5 \times 10^{-1}$ | 88 | $1.6 \times 10^{-1}$ | 90 |
| A | $1.0 \times 10^{-1}$ | 73 | $0.8 \times 10^{-1}$ | 21 |
| B | $2.0 \times 10^{-1}$ | 113 | $0.5 \times 10^{-1}$ | 42 |
| C | $2.1 \times 10^{-1}$ | 61 | $1.2 \times 10^{-1}$ | 15 |

EXAMPLE 6

A 1.0% cyclohexane solution of poly(4-methylpentene-1) was coated on the dense layer of the same supporting membrane as used in Example 5 to a thickness of 30 μm and dried at 120° C. for 10 minutes to prepare a composite membrane having an elastomeric polymer film.

Then, the elastomeric polymer film of the composite membrane was irradiated with 0.5 Mrad of an electron beam to crosslink the poly(4-methylpentene-1).

Each of the non-irradiated and irradiated composite membranes was immersed first in petroleum benzine and then in gasoline, washed with hexane, and dried in the same manner as in Example 5.

Each of the non-irradiated and irradiated membranes was determined for P($CO_2$) and α either before and after the immersion in solvents, and the results obtained are shown in Table 7 below.

TABLE 7

| Treatment | Before Immersion | | After Immersion | |
|---|---|---|---|---|
| | PO(CO) (Nm³/m² · hr · atom) | α | PO(CO) (Nm³/m² · hr · atom) | α |
| Irradiated | $1.2 \times 10^{-1}$ | 153 | $1.2 \times 10^{-1}$ | 148 |
| Non-irradiated | $2.2 \times 10^{-1}$ | 141 | $3.3 \times 10^{-1}$ | 43 |

EXAMPLE 7

The same polyimide resin solution as used in Example 1 was prepared, and in the solution was dissolved 50 parts of dioxane (flocculation value' 170) as a swelling agent per 100 parts of the polyimide to prepare a film-forming solution.

The film-forming solution was coated on polyester non-woven cloth to a thickness of 200 μm, and the cloth was dipped in isopropanol at 3° C. for 10 seconds and then in water at 3° C. to obtain a water-containing membrane having an anisotropic structure.

The resulting water-containing membrane was soaked first in ethanol and then in hexane for 3 hours, respectively, followed by air-drying at 25° C. to obtain a dried supporting membrane.

A solution of a crosslinkable silicone resin shown in Table 8 below was coated on the supporting membrane to a thickness of 50 μm, dried at 80° C. for 10 minutes, and allowed to stand at room temperature for 2 days to obtain a composite membrane (Sample Nos. 701 to 705).

Each of the resulting composite membranes was determined for rate of permeation to carbon dioxide and coefficient of $CO_2/CH_4$ separation, and the results are shown in Table 8.

EXAMPLE 8

A solution of crosslinkable silicone resin shown in Table 8 was coated on the same supporting membrane as used in Example 7 to a thickness of 50 μm. After the solvent was removed by drying, the coating film was covered with a polyethylene sheet for the purpose of conducting crosslinking effectively. The film was then irradiated with 10 Mrad of an electron beam in a nitrogen atmosphere to crosslink the silicone resin to obtain a composite membrane having a crosslinked silicone resin film (Sample Nos. 801 to 802).

Each of the resulting composite membranes was determined for rate of permeation to carbon dioxide and coefficient of $CO_2/CH_4$ sepration, and the results are shown in Table 8.

EXAMPLE 9

A 4.0% isooctane solution of one-can type RTV polydimethylsiloxane 615 was prepared, and benzoyl peroxide was added thereto. The solution was coatd on the same supporting membrane as used in Example 7 to a thickness of 50 μm and heated at 100° C. for 5 hours to crosslink the silicone resin though methylene crosslinking reaction to obtain a composite membrane (Sample No. 901). The rate of permeation to carbon dioxide and coefficient of $CO_2/CH_4$ separation of Sample 901 are shown in Table 8.

TABLE 8

| Sample No. | Silicone Resin Solution | | | Coefficient of $CO_2/CH_4$ Separation of Silicone Resin | Composite Membrane | |
|---|---|---|---|---|---|---|
| | Silicone Resin | Solvent | Concn. (wt %) | | Rate of Permeation to Carbon Dioxide (Nm³/m² · hr · atom) | Coefficient of $CO_2/CH_4$ Separation |
| 701 | SH-780*¹ | ethyl acetate | 1.0 | 4.5 | $1.6 \times 10^{-1}$ | 36 |
| 702 | SH-780 | ethyl acetate | 4.0 | 4.5 | $1.1 \times 10^{-1}$ | 51 |
| 703 | RTV-615*² | isooctane | 4.0 | 4.5 | $1.5 \times 10^{-1}$ | 62 |
| 704 | SE-9155*³ | " | 4.0 | 4.5 | $1.5 \times 10^{-1}$ | 57 |
| 705 | polydimethylsiloxane *⁴ | methyl acetate | 5.0 | 4.5 | $5.7 \times 10^{-1}$ | 52 |
| 801 | SH-780 | ethyl acetate | 4.0 | 4.5 | $1.5 \times 10^{-1}$ | 59 |
| 802 | SB-9155 | ethyl acetate | 4.0 | 4.5 | $1.8 \times 10^{-1}$ | 62 |
| 901 | RTV-615 | isooctane | 4.0 | 4.5 | $2.2 \times 10^{-1}$ | 71 |

Note:
*¹made by Toshiba Silicone Co., Ltd.
*²made by General Electric Inc.
*³made by Toray Silicone Co., Ltd.
*⁴water-induced crosslinking type (de-oxime type); curing condition: heating at 60° C. for 30 mins. and allowing to stand at room temperature for 1 day.

REFERENCE EXAMPLE

In a 500 ml-volume separable flask equipped with a stirrer, a thermometer, and side tube with a condenser were charged 46.8 g (0.20 mol) of butanetetracarboxylic acid and 0.20 mol of each of a diamine having formula:

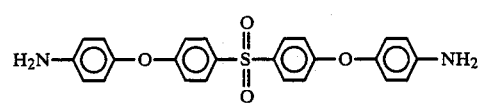

a diamine having formula:

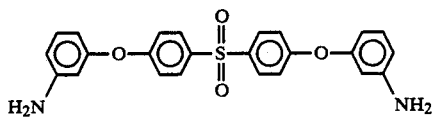

and a diamine having formula:

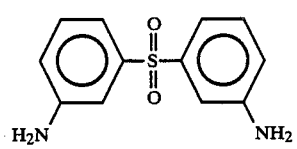

To the mixture were added 270 ml of N-methyl-2-pyrrolidone and 50 ml of xylene to dissolve the solid substances. The solution was heated at 180° C. for 30 to 40 minutes under through stirring to effect condensation reaction while removing water as the xylene azeotrope. Thereafter, the xylene was completely removed by distillation to obtain an N-methyl-2-pyrrolidone solution of the respective polyimide resin, which was used in Example 10, 11, or 12, respectively.

EXAMPLE 10

A 18% N-methyl-2-pyrrolidone solution of a polyimide resin having a repeating unit of formula:

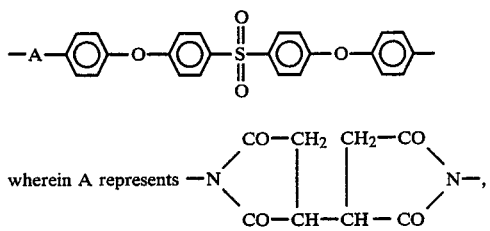

as prepared in Reference Example was coated on polyester non-woven cloth to a thickness of 200 μm. The coated cloth was dipped in an organic solvent as shown in Table 9 under prescribed conditions and then in water at 3° C. to obtain a water-containing membrane having an anisotropic structure.

Each of the water-containing membranes was soaked in ethanol and then in hexane for 3 hours, respectively, followed by air-drying at 25° C.

Each of the resulting dried membranes (Sample Nos. 1001 to 1020) was determined for rate of permeation to carbon dioxide and coefficient of $CO_2/CH_4$ separation, and the results are shown in Table 9.

EXAMPLE 11

A membrane was prepared in the same manner as in Example 10, except for using an N-methyl-2-pyrrolidone solution of polyimide-sulfone having a repeating unit of formula:

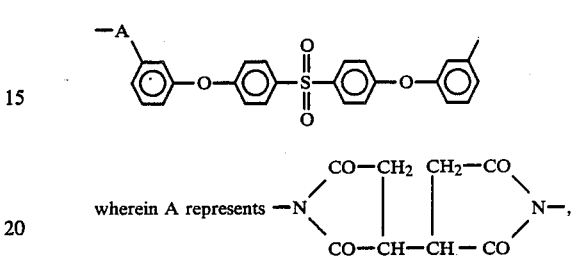

(intrinsic viscosity [η]: 0.51 dl/g) as prepared in Reference Example. Each of the resulting membranes (Sample Nos. 1101 to 1108) was determined for rate of permeation to carbon dioxide and coefficient of $CO_2/CH_4$ separation, and the resulting are shown in Table 9.

EXAMPLE 12

A membrane was prepared in the same manner as in Example 10, except for using an N-methyl-2-pyrrolidone solution of a polyimide resin having a repeating unit of formula:

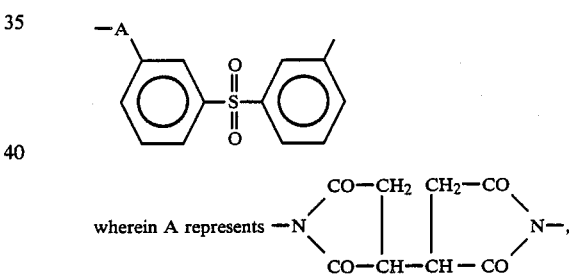

as prepared in Reference Example.

Each of the resulting membranes (Sample Nos. 1201 to 1208) was determined for rate of permeation to carbon dioxide and coefficient of $CO_2/CH_4$ separation, and the results are shown in Table 9.

TABLE 9

| Sample No. | Solvent Dipping Conditions | | | Rate of Permeation to Carbon Dioxide ($Nm^3/m^2 \cdot hr \cdot atm$) | Coefficient of $CO_2/CH_4$ Separation |
|---|---|---|---|---|---|
| | Organic Solvent | Temp. (°C.) | Time (sec) | | |
| 1001 | isopropyl alcohol | 3 | 10 | 0.61 | 56 |
| 1002 | " | " | 30 | 0.34 | 41 |
| 1003 | " | 20 | 10 | 0.57 | 41 |
| 1004 | " | " | 30 | 0.42 | 49 |
| 1005 | ethylene glycol | 3 | 10 | 9.9 | 5 |
| 1006 | " | " | 30 | 6.9 | 12 |
| 1007 | " | 20 | 10 | 3.4 | 18 |
| 1008 | " | " | 30 | 2.3 | 15 |
| 1009 | tetrahydrofuran | 3 | 10 | 8.6 | 7 |
| 1010 | " | " | 30 | 4.1 | 13 |
| 1011 | " | 20 | 10 | 7.8 | 17 |
| 1012 | " | " | 30 | 3.5 | 21 |
| 1013 | acetone | 3 | 10 | 5.4 | 26 |
| 1014 | " | " | 30 | 3.2 | 20 |
| 1015 | " | 20 | 10 | 4.1 | 22 |

TABLE 9-continued

| Sample No. | Solvent Dipping Conditions | | | Rate of Permeation to Carbon Dioxide ($Nm^3/m^2 \cdot hr \cdot atm$) | Coefficient of $CO_2/CH_4$ Separation |
|---|---|---|---|---|---|
| | Organic Solvent | Temp. (°C.) | Time (sec) | | |
| 1016 | " | " | 30 | 2.4 | 19 |
| 1017 | t-butanol | 25 | 10 | 2.2 | 35 |
| 1018 | " | " | 30 | 1.6 | 31 |
| 1019 | " | 45 | 3 | 1.9 | 19 |
| 1020 | " | " | 10 | 1.1 | 35 |
| 1101 | acetone | 3 | 10 | 8.3 | 12 |
| 1102 | " | " | 30 | 5.5 | 14 |
| 1103 | " | 20 | 10 | 6.7 | 19 |
| 1104 | " | " | 30 | 4.3 | 27 |
| 1105 | t-butanol | 25 | 10 | 3.4 | 19 |
| 1106 | " | " | 30 | 2.3 | 28 |
| 1107 | " | 45 | 3 | 2.8 | 39 |
| 1108 | " | " | 10 | 1.4 | 42 |
| 1201 | acetone | 3 | 10 | 10.2 | 1.2 |
| 1201 | " | " | 30 | 7.6 | 1.3 |
| 1203 | " | 20 | 10 | 8.2 | 11 |
| 1204 | " | " | 30 | 4.0 | 4 |
| 1205 | t-butanol | 25 | 10 | 5.0 | 8 |
| 1206 | " | " | 30 | 1.8 | 6 |
| 1207 | " | 45 | 3 | 4.9 | 13 |
| 1208 | " | " | 10 | 2.0 | 5 |

EXAMPLE 13

A membrane was prepared in the same manner as for Sample 1019 of Example 10, except that the polyimide resin solution further contained a swelling agent as shown in Table 10. Each of the resulting membranes (Sample Nos. 1301 to 1312) was determined for rate of permeation to carbon dioxide and coefficient of $CO_2/CH_4$ separation, and the results obtained are shown in Table 10.

TABLE 10

| Sample No. | Swelling Agent | | | Rate of Permeation to Carbon Dioxide ($Nm^3/m^2 \cdot hr \cdot atm$) | Coefficient of $CO_2/CH_4$ Separation |
|---|---|---|---|---|---|
| | Kind | Flocculation Value | Amount Added (part*) | | |
| 1301 | acetone | 63 | 25 | 2.5 | 63 |
| 1302 | " | " | 50 | 6.2 | 58 |
| 1303 | " | " | 100 | 4.3 | 42 |
| 1304 | " | " | 200 | 1.9 | 29 |
| 1305 | dioxane | 170 | 25 | 5.8 | 42 |
| 1306 | " | " | 50 | 10.2 | 39 |
| 1307 | " | " | 100 | 8.1 | 30 |
| 1308 | " | " | 200 | 6.0 | 27 |
| 1309 | tetrahydrofuran | 88 | 25 | 4.2 | 41 |
| 1310 | " | " | 50 | 7.9 | 40 |
| 1311 | " | " | 100 | 6.0 | 35 |
| 1312 | " | " | 200 | 4.2 | 32 |

Note:
*per 100 parts by weight of the resin.

EXAMPLE 14

The same N-methyl-2-pyrrolidone solution of a polyimide resin as used in Example 10 was coated on polyester non-woven cloth to a thickness of 200 μm. The cloth was dipped in t-butanol at 45° C. for 3 seconds and then in water at 3° C. to obtain a water-containing membrane having an anisotropic structure.

The water-containing membrane was soaked in ethanol and then in hexane for 3 hours, respectively, and air-dried at 25° C. to obtain a dried membrane as a supporting membrane.

On the supporting membrane was coated an elastomeric polymer solution as shown in Table 11 to a thickness of 30 μm, followed by drying at 80° C. for 30 minutes to obtain a composite membrane.

Each of the resulting composite membranes (Sample Nos. 1401 to 1404) was determined for rate of permeation to carbon dioxide and coefficient of $CO_2/CH_4$ separation, and the results obtained are shown in Table 11.

TABLE 11

| Sample No. | Elastomeric Polymer Solution | | | Coefficient of $CO_2CH_4$ Separation of Elastomeric Polymer | Composite Membrane | |
|---|---|---|---|---|---|---|
| | Elastomeric Polymer | Solvent | Concn. (wt %) | | Rate of Permeation to Carbon Dioxide ($Nm^3/m^2 \cdot hr \cdot atm$) | Coefficient of $CO_2/CH_4$ Separation |
| 1401 | poly (4-methylpentene-1) | cyclohexane | 1.0 | 5.4 | 1.10 | 192 |
| 1402 | butadiene-sytrene copolymer | toluene | 1.0 | 18 | 0.92 | 133 |

TABLE 11-continued

| | Elastomeric Polymer Solution | | | Coefficient of $CO_2CH_4$ Separation of Elastomeric Polymer | Composite Membrane | |
|---|---|---|---|---|---|---|
| | | | | | Rate of Permeation to Carbon Dioxide ($Nm^3/m^2 \cdot hr \cdot atm$) | Coefficient of $CO_2/CH_4$ Separation |
| Sample No. | Elastomeric Polymer | Solvent | Concn. (wt %) | | | |
| 1403 | polyisobutylene | isooctane | 0.5 | 11 | 0.55 | 94 |
| 1404 | isoprene-isobutylene copolymer | toluene | 1.0 | 12 | 0.84 | 62 |

EXAMPLE 15

Composite membranes (Sample Nos. 1501 to 1506) were prepared in the same manner as in Example 14, except for using each of the elastomeric polymer solutions shown in Table 12 below. In the preparation of Samples 1505 and 1506, the conditions for film formation on the supporting membrane were altered according to the footnote of Table 12.

Each of the resulting composite membranes was determined for rate of permeation to carbon dioxide and coefficient of $CO_2/CH_4$ separation, and the results obtained are shown in Table 12.

EXAMPLE 17

A 1.0% solution of poly(4-methylpentene-1) in cyclohexane was prepared. The solution was coated on the same supporting membrane as used in Example 14 to a thickness of 30 μm and dried at 120° C. for 10 minutes to obtain a composite membrane having an elastomeric polymer film.

The elastomeric polymer film was irradiated with an electron beam of 0.5 Mrad in a nitrogen atmosphere to crosslink the poly(4-methylpentene-1).

Each of the non-irradiated composite membrane and the irradiated composite membranes was determined

TABLE 12

| | Elastomeric Polymer Solution | | | Coefficient of $CO_2/CH_4$ Separation of Elastomeric Polymer | Composite Membrane | |
|---|---|---|---|---|---|---|
| | | | | | Rate of Permeation to Carbon Dioxide ($Nm^3/m^2 \cdot hr \cdot atm$) | Coefficient of $CO_2/CH_4$ Separation |
| Sample No. | Elastomeric Polymer | Solvent | Concn. (wt %) | | | |
| 1501 | polyester polyol | chloroform | 1.0 | 10 | 0.44 | 98 |
| 1502 | polyurethane polyol | tetrahydrofuran | 1.0 | 11 | 0.37 | 131 |
| 1503 | polyurethane polyester | tetrahydrofuran | 1.0 | 19 | 0.50 | 120 |
| 1504 | polyamide polyether | chloroform | 0.5 | 9 | 0.79 | 134 |
| 1505 | epoxy resin* | toluene | 5.0 | 15 | 0.12 | 155 |
| 1506 | ethyl cellulose** | chloroform | 2.0 | 18 | 0.68 | 134 |

Note:
*Comprised 100 parts of Epon 828 (made by Shell Chemical), 10 parts of a curing agent CIBN (carboxyl-terminated butadiene-acrylonitrile copolymer), and 5 parts of tetramethylguanidine; curing conditions: heating at 180° C. for 1 hour.
**Heated at 60° C. for 30 minutes.

EXAMPLE 16

A solution of an elastomeric polymer containing a radical generator or a polyisocyanate as a crosslinking agent as shown in Table 5 was coated on the same supporting membrane as used in Example 14 to a thickness of 30 μm and dried at 120° C. for 10 minutes to obtain a composite membrane having a crosslinked elastomeric polymer film.

Each of the resulting composite membranes (Sample Nos. 1601 to 1603) was determined for rate of permeation to carbon dioxide [$P(CO_2)$] and coefficient of $CO_2/CH_4$ separation ($\alpha$), and the results obtained are shown in Table 13.

TABLE 13

| | Gas Permeability Before Immersion in Solvent | | Gas Permeability After Immersion in Solvent | |
|---|---|---|---|---|
| Sample No. | P(CO) ($Nm^3/m^2 \cdot hr \cdot atm$) | $\alpha$ | P(CO) ($Nm^3/m^2 \cdot hr \cdot atm$) | $\alpha$ |
| 1601 | 0.88 | 67 | 0.92 | 71 |
| 1602 | 1.08 | 152 | 1.11 | 145 |
| 1603 | 1.22 | 90 | 1.02 | 92 | for rate of permeation to carbon dioxide and coefficient of $CO_2/CH_4$ separation, and the results obtained are shown in Table 14.

Then, each of the membranes was immersed in petroleum benzine and then in gasoline, washed with hexane, and dried in the same manner as in Example 16. The thus treated membrane was determined for rate of permeation to carbon dioxide and coefficient of $CO_2/CH_4$ separation, and the results obtained are shown in Table 14.

TABLE 14

| | Gas Permeability Before Immersion in Solvent | | Gas Permeability After Immersion in Solvent | |
|---|---|---|---|---|
| Sample | P(CO) ($Nm^3/m^2 \cdot hr \cdot atm$) | $\alpha$ | P(CO) ($Nm^3/m^2 \cdot hr \cdot atm$) | $\alpha$ |
| Irradiated | 0.68 | 161 | 0.76 | 152 |
| Non-irradiated | 1.31 | 139 | 1.33 | 52 |

EXAMPLE 18

A crosslinkable silicone resin solution shown in Table 15 was coated on the same supporting membrane as used in Example 14 to a thickness of 50 μm, dried at 80° C. for 10 minutes, and allowed to stand at room temperature for 2 days to obtain a composite membrane (Sample Nos. 1801 to 1805).

Each of the composite membranes was determined for rate of permeation to carbon dioxide and coefficient of $CO_2/CH_4$ separation, and the results obtained are shown in Table 15.

EXAMPLE 19

A crosslinkable silicone resin solution shown in Table 15 was coated on the same supporting membrane as used in Example 14 to a thickness of 50 μm and dried to remove the solvent. In order to conduct crosslinking efficiently, the silicone resin film was covered with a polyethylene sheet, and the film was irradiated with an electron beam of 10 Mrad in a nitrogen atmosphere to crosslink the silicone resin to obtain a composite membrane (Sample Nos. 1901 to 1902).

Each of the composite membranes was determined for rate of permeation to carbon dioxide and coefficient of $CO_2/CH_4$ separation, and the results obtained are shown in Table 15.

EXAMPLE 20

An isooctane solution of one-can type RTV polydimethylsiloxane 615 as shown in Table 15 was prepared, and benzoyl peroxide was added thereto. The resulting solution was coated on the same supporting membrane as used in Example 14 to a thickness of 50 μm and heated at 100° C. for 5 hours to crosslink the silicone resin to obtain a composite membrane (Sample No. 2001).

The resulting composite membrane was determined for rate of permeation to carbon dioxide and coefficient of $CO_2/CH_4$ separation, and the results are shown in Table 15.

C. for 30 minutes to obtain a composite membrane (Sample No. 2101).

A composite membrane was prepared in the same manner as described above, except for using the same polyimide resin as used in Example 12 (Sample No. 2102).

Each of the resulting composite membranes was determined for rate of permeation to carbon dioxide and coefficient of $CO_2/CH_4$ separation, and the results obtained are shown in Table 16.

TABLE 16

| Sample No. | Gas Permeability P(SO) (Nm3/m2 · hr · atm) | α |
|---|---|---|
| 2101 | 0.52 | 129 |
| 2002 | 0.36 | 99 |

While the invention has been described in detail and with reference to specific embodiments thereof, it will be apparent to one skilled in the art that various changes and modifications can be made therein without departing from the spirit and scope thereof.

What is claimed is:

1. A process for separating methane from a gaseous mixture containing methane and carbon dioxide by concentration, which comprises contacting said gaseous mixture with a membrane comprising a film of a polyimide resin having a repeating unit represented by formula (I):

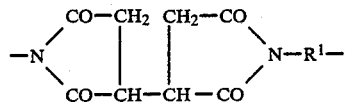

wherein $R^1$ represents a divalent aromatic, alicyclic or

TABLE 15

| Sample No. | Silicone Resin Solution | | | Coefficient of $CO_2/CH_4$ Separation of Silicone Resin | Composite Membrane | |
|---|---|---|---|---|---|---|
| | Silicone Resin | Solvent | Concn. (wt %) | | Rate of Permeation to Carbon dioxide (Nm$^3$/m$^2$ · hr · atm) | Coefficient of $CO_2/CH_4$ Separation |
| 1801 | SH-780*1 | ethyl acetate | 1.0 | 4.5 | 0.43 | 84 |
| 1802 | SH-780 | ethyl acetate | 4.0 | 4.5 | 0.38 | 91 |
| 1803 | RTV-615*2 | isooctane | 4.0 | 4.5 | 0.56 | 96 |
| 1804 | SE-9155*3 | " | 4.0 | 4.5 | 0.54 | 102 |
| 1805 | polydimethylsiloxane*4 | methyl acetate | 5.0 | 4.5 | 0.81 | 125 |
| 1901 | SH-780 | ethyl acetate | 4.0 | 4.5 | 0.66 | 69 |
| 1902 | SE-9155 | ethyl acetate | 4.0 | 4.5 | 0.79 | 78 |
| 2001 | RTV-615 | isooctane | 4.0 | 4.5 | 0.64 | 92 |

Note:
*1 made by Toshiba Silicone Co., Ltd.
*2 made by General Electric Inc.
*3 made by Toray Silicone Co., Ltd.
*4 water-induced crosslinking type (de-oxime type); curing condition: heating at 60° C. for 30 mins. and allowing to stand at room temperature for 1 day.

EXAMPLE 21

A dried membrane was prepared in the same manner as in Example 14, except for using the same polyimide resin as used in Example 11. A 1% solution of poly(4-methylpentene-1) was coated on the dense layer of the dried membrane to a thickness of 30 μm and dried at 80° aliphatic hydrocarbon group, or a divalent organic group composed of these hydrocarbon groups linked via a divalent organic linking group, to selectively pass carbon dioxide through said membrane.

2. A process as claimed in claim 1, wherein $R^1$ represents an aromatic hydrocarbon group or an aromatic hydrocarbon group composed of two aromatic hydrocarbon groups connected by an organic linking group.

3. A process as claimed in claim 2, wherein wherein $R^1$ represents an aromatic hydrocarbon group composed of two aromatic hydrocarbon groups connected via an alkylene group or an ether group.

4. A process as claimed in claim 3, wherein

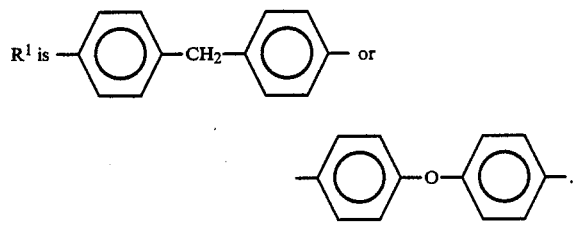

5. A process as claimed in claim 2, wherein the organic linking group is selected from the class consisting of alkylene, ether, sulfido, sulfo, amido, ester, urethane, and urea groups.

6. A process as claimed in claim 1, wherein $R^1$ represents a divalent organic group containing a sulfo group represented by formula (II):

$$-R^2-SO_2-R^3- \quad (II)$$

wherein $R^2$ and $R^3$ each represents a divalent aromatic, alicyclic or aliphatic hydrocarbon group, or a divalent organic group composed of these hydrocarbon groups linked via a divalent organic linking group.

7. A process as claimed in claim 6, wherein both $R^2$ and $R^3$ represent an aromatic hydrocarbon group or an aromatic hydrocarbon group composed of two aromatic hydrocarbon groups linked via an organic linking group.

8. A process as claimed in claim 7, wherein the organic linking group is selected from the class consisting of alkylene, ether, and sulfido groups.

9. A process as claimed in claim 6, wherein

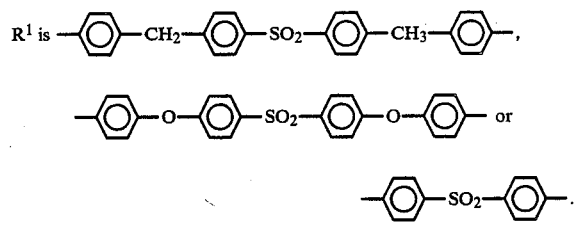

10. A process as claimed in claim 6, wherein the divalent organic linking group is selected from the class consisting of alkylene, ether, sulfido, and polyoxyalkylene groups.

11. A process as claimed in claim 1, wherein said polyimide resin has an intrinsic viscosity $[\eta]$ of from 0.4 to 2 dl/g as measured in N-methyl-2-pyrrolidone at 30° C.

12. A process as claimed in claim 1, wherein said film of a polyimide resin is obtained by a process comprising preparing a film-forming solution comprised of the polyimide resin having the repeating unit of formula (I), a water-miscible organic solvent, and at least one liquid swelling agent having a flocculation value for said polyimide resin in the range of from 50 to 200 and having a boiling point of from 50° to 120° C. at atmospheric pressure which is selected from the group consisting of cyclic ethers, aliphatic ketones, alicyclic ketones, lower aliphatic carboxylic acids, and lower aliphatic carboxylic acid lower alkyl esters, the flocculation value of said swelling agent being defined as the minimum number of milliliters of the swelling agent added to 50 ml of a 2% by weight solution of the polyimide resin in N-methylpyrrolidone causing white turbidity due to flocculation of the resin at 25° C., coating the film-forming solution on a base, dipping the coated base in an organic solvent incapable of dissolving said polyimide resin but miscible with both said water-miscrible organic solvent and water and then in water to obtain a water-containing polyimide membrane having an anisotropic structure, and drying the polyimide membrane.

13. A process as claimed in claim 12, wherein said water-miscible organic solvent is selected from the group consisting of an N-alkyl-2-pyrrolidone, an N-alkyl-2-piperidone, a dialkylacetamide, and a dialkylformamide.

14. A process as claimed in claim 12, wherein said water-miscible organic solvent is N-methyl-2-pyrralidone.

15. A process as claimed in 12, wherein said solvent incapable of dissolving the polyimide resin but miscible with both of the water-miscible organic solvent and water is selected from the group consisting of lower aliphatic alcohols, alcohols having a cyclic structure, ketones, esters of formic acid, acetic acid, lactic acid or phosphoric acid, polyhydric alcohols and derivatives thereof, ethers, and nitriles.

16. A process as claimed in claim 12, wherein said dipping in the organic solvent is at a temperature of from 0° to 100° C. for 5 minutes or less.

17. A process as claimed in claim 12, wherein said swelling agent is selected from the group consisting of tetrahydrofuran, dioxane, acetone, methyl ethyl ketone, diethyl ketone, cyclohexanone, acetic acid, formic acid, methyl formate, ethyl formate, and methyl acetate.

18. A process as claimed in claim 12, wherein said swelling agent is used in an amount of from 30 to 300 parts by weight per 100 parts by weight of the polyimide resin.

19. A process as claimed in claim 1, wherein said membrane further comprises an elastomeric polymer film formed on said polyimide resin membrane.

20. A process as claimed in claim 19, wherein said polyimide resin film has a coefficient of $CO_2/CH_4$ separation of at least 0.7.

21. A process as claimed in claim 19, wherein said elastomeric polymer film has a coefficient of $CO_2/CH_4$ separation of at least 3 and a softening point of at least 50° C.

22. A process as claimed in claim 19, wherein said elastomeric polymer film is a crosslinked elastomeric polymer film.

23. A process as claimed in claim 22, wherein said crosslinked elastomeric polymer film is formed by crosslinking a crosslinkable silicone resin.

24. A process as claimed in claim 23, wherein said crosslinkable silicone resin has an average molecular weight of from 10,000 to 300,000.

25. A process as claimed in claim 1, wherein the divalent organic linking group is selected from the class consisting of alkylene, ether, sulfido, sulfo, amido, ester, urethane, urea, and polyoxyalkylene groups.

* * * * *